United States Patent [19]
Chen et al.

[11] Patent Number: 6,110,944
[45] Date of Patent: *Aug. 29, 2000

[54] LTA$_4$, HYDROLASE INHIBITORS

[75] Inventors: Barbara Baosheng Chen, Glenview, Ill.; Helen Chen, Livingston, N.J.; Mark Andrew Russell, Gurnee, Ill.

[73] Assignee: G. D. Searle & Co., Chicago, Ill.

[ * ] Notice: This patent issued on a continued prosecution application filed under 37 CFR 1.53(d), and is subject to the twenty year patent term provisions of 35 U.S.C. 154(a)(2).

[21] Appl. No.: 08/814,899

[22] Filed: Mar. 12, 1997

[51] Int. Cl.$^7$ ............... A61K 31/445; C07D 211/60; C07D 207/04; C07C 69/76
[52] U.S. Cl. ............... 514/330; 514/428; 514/534; 514/539; 514/633; 514/637; 546/227; 548/569; 548/571; 560/8; 560/24; 560/35; 564/229; 564/247
[58] Field of Search ............... 514/428, 330, 514/534, 539, 637, 633; 548/569, 571; 546/227; 560/8, 24, 35; 564/229, 247

[56] References Cited

U.S. PATENT DOCUMENTS

| | | | |
|---|---|---|---|
| 2,676,968 | 4/1954 | Burtner et al. | 260/294.7 |
| 2,811,526 | 10/1957 | Burtner et al. | 260/294.7 |
| 4,943,584 | 7/1990 | Theobald et al. | 514/380 |
| 5,585,492 | 12/1996 | Chandrakumar et al. | 546/227 |
| 5,700,816 | 12/1997 | Isakson et al. | 514/326 |
| 5,719,306 | 2/1998 | Chandrakumar et al. | 560/19 |
| 5,723,492 | 3/1998 | Chandrakumar et al. | 514/539 |

FOREIGN PATENT DOCUMENTS

| | | |
|---|---|---|
| 287 959 | 10/1988 | European Pat. Off. . |
| 287959 | 10/1988 | European Pat. Off. . |
| 4121849 | 1/1993 | Germany . |
| WO 9610999 | 4/1996 | WIPO . |
| WO 9611192 | 4/1996 | WIPO . |
| WO 9641625 | 12/1996 | WIPO . |

OTHER PUBLICATIONS

Cavallini et al., IL FARMACO, vol. XI, No. 4, Apr. 1956, pp. 378–388.
Labaudiniere, R. et al., J. Med. Chem. vol. 35 (17), pp. 3156–3169 (1992).
Yuan, J.H. et al., Drug Metab. Dispos., vol. 24 (10), pp. 1124–1133 (1996).
Cavallini, V.G. et al., Farmaco Ed. Sci. vol. 11, pp. 378–388 (1956).
Chem. Abstracts, vol. 117(11), Abstr. No. 111411, Sep. 14, 1992.
Chem. Abstracts, vol. 126(1), Abstr. No. 302, Jan. 1, 1997.
Chem. Abstracts, vol. 53(10), Abstr. No. 9194, May 25, 1959.

*Primary Examiner*—Richard L. Raymond
*Assistant Examiner*—Tamthom N. Truong
*Attorney, Agent, or Firm*—Fitzpatrick, Cella, Harper & Scinto

[57] ABSTRACT

The present invention provides compounds having the structure

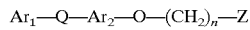

$$Ar_1—Q—Ar_2—O—(CH_2)_n—Z$$

and pharmaceutically acceptable salts and stereoisomers thereof that are useful in the treatment of inflammatory diseases which are mediated by $LTB_4$ production, such as psoriasis, ulcerative colitis, IBD, and asthma.

4 Claims, No Drawings

LTA$_4$ HYDROLASE INHIBITORS

FIELD OF THE INVENTION

This invention relates generally to anti-inflammatory compounds and pharmaceutical compositions, and more particularly to anti-inflammatory compounds and compositions which are capable of inhibiting leukotriene A$_4$ hydrolase.

BACKGROUND OF THE INVENTION

LTA$_4$ hydrolase is a requisite enzyme in the biosynthetic pathway leading to LTB$_4$ formation. LTB$_4$ is a proinflammatory compound. R. Lewis, et al., *N. Engl. J. Med.* 323, 645–655 (1990) have demonstrated that LTB$_4$ is a potent granulocyte agonist inducing chemotaxis, aggregation, degranulation, adherence and priming of inflammatory cells for induction by other agonists. Binding of LTB$_4$ to receptors is stereospecific with two distinct classes of binding sites. A. Lin, et al., *Prostaglandins* 28, 837–849 (1984). A high affinity site [4–5×10$^{-10}$ M] mediates chemotaxis and chemokinesis while lower affinity sites [0.6–5×10$^{-7}$ M] stimulate granular secretion and oxidative burst. The LTB$_4$ receptor is associated with a GTP-binding protein that regulates affinity and transduces signals. T. Schepers, et al., *J. Biol. Chem.* 267, 159–165 (1992). Elevated LTB$_4$ levels have been reported for many diseases. Most prominently, elevated LTB$_4$ levels have been correlated to the pathology of inflammatory bowel disease (IBD) including Crohn's disease and ulcerative colitis and in psoriasis. P. Sharon, et al., *Gastroent.* 86, 453–460; K. Lauritsen, et al., *Gastroent.* 95, 11–17 (1989); S. Brain, et al., *Br. J. Pharm.,* 83, 313–317 (1984). Other properties of LTB$_4$ which may contribute to disease processes are: stimulation of mucus secretion; stimulation of cytokine production; and the ability to act synergistically with other inflammatory mediators such as prostaglandins and cysteinyl leukotrienes thereby amplifying the inflammatory process.

B. Samuelsson, et al., *J. Biol Chem.,* 264, 19469–19472 (1989) have shown that LTB$_4$ biosynthesis from arachidonic acid involves the action of 2 enzymes, 5-lipoxygenase [5-LO] and LTA$_4$ hydrolase. 5-LO transforms arachidonic acid to 5-HPETE and subsequent formation of LTA$_4$, which is an unstable allylic epoxide intermediate which is enzymatically hydrolyzed by LTA$_4$ hydrolase to form the dihydroxy acid LTB$_4$.

LTA$_4$ hydrolase is distinct from cytosolic and microsomal epoxide hydrolases based on strict substrate requirements, product formation [5(S),12(R) vs. 5(S),6(R)] for mouse liver cytosolic epoxide hydrolase, and lack of inhibition by inhibitors of cytosolic epoxide hydrolase. LTA$_4$ hydrolase appears to be ubiquitously distributed in mammalian tissues even in cell types that do not express 5-LO, suggesting the importance of transcellular metabolism of LTA$_4$. While peptidomimetic compounds such as bestatin and captopril have been shown to exhibit LTA$_4$ hydrolase inhibitory activity, they are not able to satisfy the requirement of a small organic compound which is capable of cellular penetration. It would therefore be very advantageous to be able to provide low molecular weight inhibitors of LTB$_4$ biosynthesis which preferably exhibit oral activity in vivo at desirably low concentrations.

SUMMARY OF THE INVENTION

Applicants have now discovered that compounds having the structure:

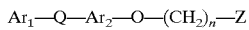

and pharmaceutically acceptable salts and stereoisomers thereof possess LTA$_4$ hydrolase inhibitor activity, wherein Ar$^1$ is an aryl moiety selected from the group consisting of:

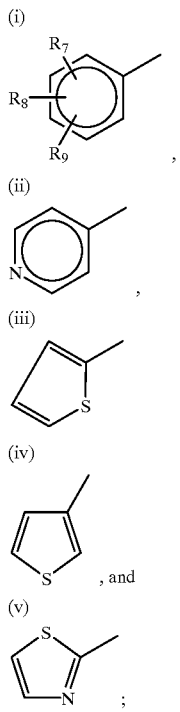

Ar$^2$ is an aryl moiety selected from the group consisting of phenyl, mono-, di-, and tri-substituted phenyl, wherein the substituents are selected from the group consisting of Cl, Br, F, CF$_3$, lower alkyl, lower alkoxy, NH$_2$, NO$_2$, and OH;

Q is selected from the group consisting of:
 (i) —O—;
 (ii) —CH$_2$—,
 (iii) —OCH$_2$—,
 (iv) —CH$_2$O—,
 (v) —NH—;
 (vi) —NHCH$_2$—,
 (vii) —CH$_2$NH—,
 (viii) —CF$_2$—m
 (ix) —CH=CH—,
 (x) —CH$_2$CH$_2$—, and
 (xi) carbon—carbon single bond;

n=1, 2 or 3;

Z is

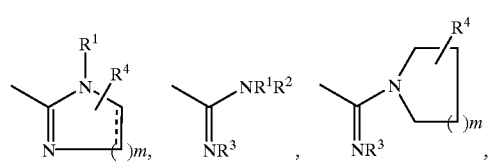

-continued

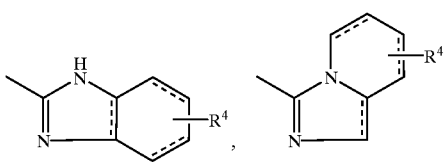

wherein
R[1], R[2] and R[3] are independently H, OH, lower alkyl, lower alkoxy, allyl, cyclic alkyl or $(CH_2)_p$—$CO_2R^5$ wherein p is an integer from 1 to 6;
R[4] is H, $CO_2R^5$, $CONH_2$, or COOH;
R[5] is H, lower alkyl, lower alkoxy, allyl or benzyl;
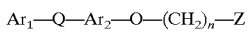 represents a single or double bond; and
m is 1 or 2.

DETAILED DESCRIPTION

In one of its embodiments, the present invention entails compounds having the structure:

$$Ar_1—Q—Ar_2—O—(CH_2)_n—Z$$

and pharmaceutically acceptable salts and stereoisomers thereof, wherein $Ar_1$, Q, $Ar_2$, Z, and n are as defined hereinbefore. In a preferred embodiment, the compounds of the present invention have the structure:

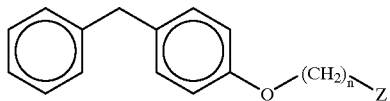

The compounds of the present invention, in several embodiments, may comprise a carboxylic acid or ester moiety. It will be appreciated by those of ordinary skill in the art
that a compound of the present invention comprising an ester moiety is readily converted, in vivo, especially when administered orally, into its corresponding carboxylic acid form. The ester-containing compounds of the present invention are therefore prodrugs of their carboxylic acid form.

In another of its aspects, the invention entails pharmaceutical composition comprising a pharmacologically effective amount of one or more of the compounds defined above and a pharmaceutically acceptable carrier.

In still another of its embodiments the present invention involves a method for treating a mammal exhibiting an LTB4 mediated inflammatory condition comprising administering to the mammal a pharmacologically effective amount of one or more of the compounds defined above.

The term "lower alkyl" means straight or branched chain alkyl having 1 to 6 carbon atoms such as methyl, ethyl, propyl, butyl, pentyl, hexyl and the branched chain isomers thereof. The term "lower alkoxy" means straight or branched chain alkoxy having 1 to 6 carbon atoms such as methoxy, ethoxy, propoxy, butoxy, pentoxy, hexoxy and the branched chain isomers thereof. The term "cyclic alkyl" as used herein refers to non-aromatic alkyl ring structures, including multi-ring structures such as bicyclic and tricyclic rings, having between 5 and 20 carbon atoms. The term "allyl" as used herein means the 1-propenyl radical, —$CH_2$—$CH_2$=$CH_2$. The term "halo" or "halogen" means fluoro, chloro, bromo, or iodo.

Included within the classes and subclasses of compounds defined above are isomeric forms of the described compounds including diastereoisomers, enantiomers and tautomeric forms of the described compounds. Pharmaceutically acceptable salts of such compounds are also included as well as pharmaceutically acceptable salts of such isomers and tautomers.

In the structures disclosed herein, a bond drawn across a bond in a ring indicates that the bond can be to any available atom of the ring structure.

The expression "pharmaceutically acceptable salts" is intended to include those salts capable of being formed with the compounds of the present invention without materially altering the chemical structure or pharmacological properties thereof. Such salts can be inorganic and organic cations or acid addition salts, and included, but are not limited to, sodium, potassium, calcium, ammonium, alkylammonium, quaternary ammonium, triethanolamine, lysine, hydrochloride, hydrobromide, and others well known to those of ordinary skill in the art. The foregoing salts are prepared in the conventional manner by neutralization of the compounds defined above with the desired base or acid.

The compounds of the present invention can be administered to a subject in such oral dosage forms as tablets, capsules, pills, powders, granules, elixirs or syrups, as well as aerosols for inhalation. Likewise, administration may be effected intravascularly, subcutaneously, or intramuscularly using dosage forms known to those of ordinary skill in the pharmaceutical arts. In general, the preferred form of administration is oral. An effective but non-toxic amount of the compound is employed in treatment. The dosage regimen utilizing the present compounds is selected in accordance with a variety of factors including the type, age, weight, sex and medical condition of the patient; the severity of the condition to be ameliorated; and the route of administration. A physician of ordinary skill can readily determine and prescribe a "pharmaceutically effective amount" of one or more of the compounds defined above, that is, the effective amount of a compound required to prevent, treat or arrest the progress of the condition. Dosages of the compounds of the present invention will range generally between 0.1 mg/kg/day to about 100 mg/kg/day and preferably between about 0.5 mg/kg/day to about 50 mg/kg/day when administered to a subject suffering from allergic or hypersensitivity reactions or inflammation. The compounds may also be administered transdermally or topically to treat proliferative skin conditions such as psoriasis. The daily dosage may be administered in a single dose or in equal divided doses, for example, three to four times daily. The "subject" is typically a mammal and, in particular, a human patient.

As used herein the phrase "$LTA_4$ hydrolase inhibitor" means a compound that is capable of exhibiting an $IC_{50}$ of less than 1 mM in an in vitro assay employing 10 μg/ml of $LTA_4$ hydrolase enzyme (specific activity 600 nMoles $LTB_4$/min/mg of enzyme) in the presence of 25 μM substrate ($LTA_4$) in a total reaction volume of 100 μl.

In the pharmaceutical compositions and methods of the present invention, at least one of the active compounds defined above or a pharmaceutically acceptable salt thereof will typically be administered in admixture with suitable pharmaceutical diluents, excipients or carriers (collectively referred to herein as "carrier materials") suitably selected with respect to the intended form of administration and consistent with conventional pharmaceutical practices. For example, the pharmaceutical compositions of this invention can be administered as oral tablets, capsules, elixirs, syrups and the like. For oral administration in the form of tablets or capsules, the active drug component may be combined with any oral non-toxic pharmaceutically acceptable inert carrier such as lactose, starch, sucrose, cellulose, magnesium stearate, dicalcium phosphate, calcium sulfate, mannitol and the like; for oral administration in liquid form, the active drug component may be combined with any oral non-toxic pharmaceutically acceptable inert carrier such as ethanol and the like. Moreover, when desired or necessary, suitable binders, lubricants, disintigrating agents and coloring agents can also be incorporated in the mixture. Suitable binders include starch, gelatin, natural sugars, corn sweeteners, natural and synthetic gums such as acacia, sodium alginate, carboxymethylcellulose, polyethylene glycol and waxes. Lubricants for use in these dosage forms include boric acid, sodium benzoate, sodium acetate, sodium chloride and the like. Disintigrators include, without limitation, starch, methylcellulose, agar, bentonite, guar gum and the like.

By virtue of their activity as $LTA_4$ hydrolase inhibitors, the compounds defined above are useful in treating inflammatory conditions mediated by $LTB_4$ production in mammals such as psoriasis, contact and atropic dermatitis, Crohn's disease, ulcerative colitis, inflammatory bowel disease, multiple sclerosis, ankylosing spondylitis, arthritis, asthma and the like. Similarly, the compounds defined above can be used in preventing recurring inflammatory attacks. A physician or veterinarian of ordinary skill can readily determine whether a subject exhibits the inflammatory condition. A preferred utility relates to treatment of ulcerative colitis.

Among the compounds of the present invention are the following:

α-[[4-(phenylmethyl)phenoxy]methyl]-1-piperidinemethanimine, monohydrochloride;

α-[[4-(phenylmethyl)phenoxy]methyl]-1-pyrrolidinemethanimine, monohydrochloride;

ethyl 1-[1-imino-2-[4-(phenylmethyl)phenoxy]ethyl]-4-piperdinecarboxylate, monohydrochloride;

ethyl 3-[[1-imino-2-[4-(phenylmethyl)phenoxy]ethyl]amino]propanoate, monohydrochloride;

4,5-dihydro-2-[[4-(phenylmethyl)phenoxy]methyl]-1H-imidazole;

1-[1-imino-2-[4-(phenylmethyl)phenoxy]ethyl-4-piperidinecarboxyamide;

1-imino-2-[4-(phenylmethyl)phenoxy]ethanamine;

α-[3-[4-(phenylmethyl)phenoxy]propyl]-1-piperidinemethanimine, monohydrochloride;

4,5-dihydro-2-[3-[4-(phenylmethyl)phenoxy]propyl]-1H-imidazole;

3a,4,5,6,7,7a-hexahydro-2-[[4-(phenylmethyl)phenoxy]propyl]-1H-benzimidazole;

2-[4-(phenylmethyl)phenoxy]-N-(tricyclo[3.3.1.1 3,7]decan-2-yl)ethanimidine, monohydrate;

N'-hydroxy-2-[4-(phenylmethyl)phenoxy]ethanimidamide.

The compounds of the invention are prepared from readily available starting materials by any of the following alternate processes in a conventional manner. The following reaction schemes describe methods which can be employed for preparing the compounds defined above, including starting materials, intermediates and reaction conditions. The following terms, as used herein, have the following definitions:

| | |
|---|---|
| NMMO | N-methylmorpholine-N-oxide |
| Me | methyl |
| SitBuMe$_2$ | t-butyldimethylsilyl |
| nBuLi | n-butyllithium |
| THF | tetrahydrofuran |
| Et$_2$O | diethyl ether |
| EtOH | ethyl alcohol |
| Pd/C | palladium on carbon |
| TFA | trifluoroacetic acid |
| Et$_3$SiH | triethylsilane |
| TBAF | tetrabutylammonium fluoride |
| DMF | dimethylformamide |
| nBu$_4$NBr | tetra-n-butylammonium bromide |
| TsCl | tosylchloride or p-toluenesulfonyl-chloride |
| TsO | tosylate or p-toluenesulfonate |
| MeOH | methyl alcohol |
| AcOH | acetic acid |
| Bn | benzyl |
| DEAD | diethylazodicarboxylate |
| Ph$_3$P | triphenylphosphine |
| MCPBA | metachloroperbenzoic acid |
| LAH | lithium aluminum hydride |
| TsOH | tosic acid or p-toluenesulfonic acid |
| LDA | lithium diisopropylamide |
| DSC | disuccinylcarbonate |
| nBuOH | n-butyl alcohol |
| TFAA | trifluoroacetic anhydride |
| Me$_3$SnN$_3$ | trimethyl-tin azide |
| TMS | trimethyl silyl |
| Ac$_2$O | acetic anhydride |
| Ac | acetate |
| EtOAc | ethyl acetate |
| Hep | heptane |

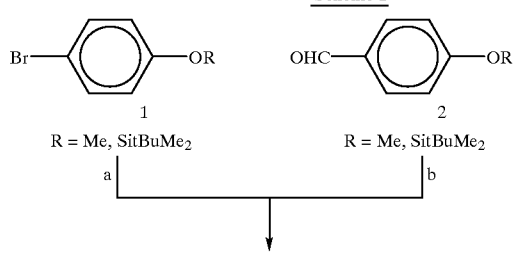

Scheme 1

-continued

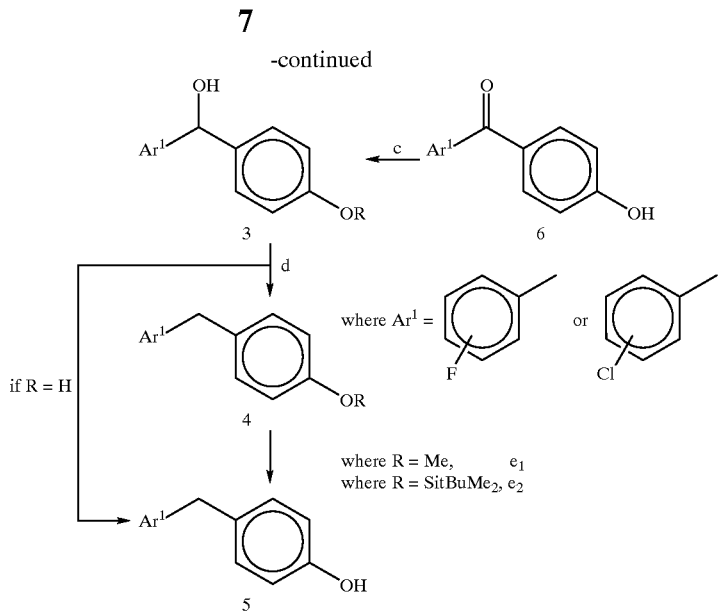

a) nBuLi, THF, -78° C.; Ar¹CHO.
b) Ar¹Li or Ar¹MgBr, Et₂O, -78° C.
c) EtOH, NaBH₄.
d) EtOH, 4% Pd/C, H₂ or CH₂Cl₂, TFA, Et₃SiH.
e¹) BBr₃, CH₂Cl₂, -78° C.
e²) THF, TBAF.

Scheme 1 shows methods for producing compounds having the structure

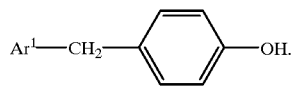

Scheme 1 shows two related precursor compounds (1, 2) which may be employed as a starting material. Compound 1 is an alkylated or silylated derivative of p-bromophenol. A convenient starting material 1 is 1-bromo,4-methoxybenzene (i.e., R is methyl). On the other hand, compound 1 may be readily provided by silylation of p-bromophenol with t-butyldiphenylsilyl chloride or other silylating agents. In either event, compound 1 may be reacted with tert-butyl lithium in an ethereal solvent at low temperature, such as in THF at −78° C., and quenched with an arylaldehyde (Ar¹CHO) to yield compound 3. Similarly, starting from compound 2, a p-methoxybenzaldehyde or a silylated derivative of p-hydroxybenzaldehyde may be employed. Compound 2 may be reacted with an aryl lithium (Ar¹Li) or aryl magnesium bromide (Ar¹MgBr) to yield compound 3. Regardless of which route is chosen, compound 3 is reduced, e.g., by hydrogenation over palladium on carbon or with triethylsilane, to provide compound 4. Compound 4 is readily deprotected using TBAF in THF (desilylation) or using BBr₃ in methylene chloride at −78° C. (dealkylation) to provide compound 5, 4-hydroxydiphenylmethane.

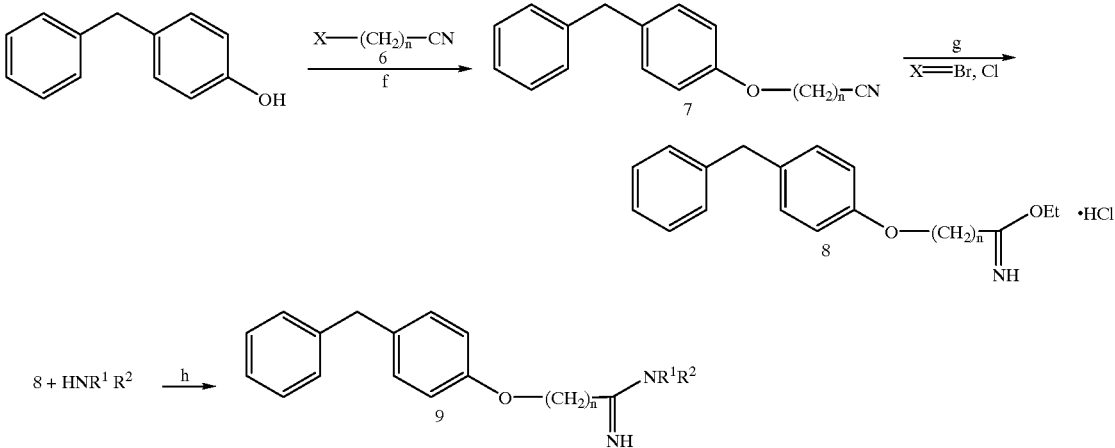

-continued

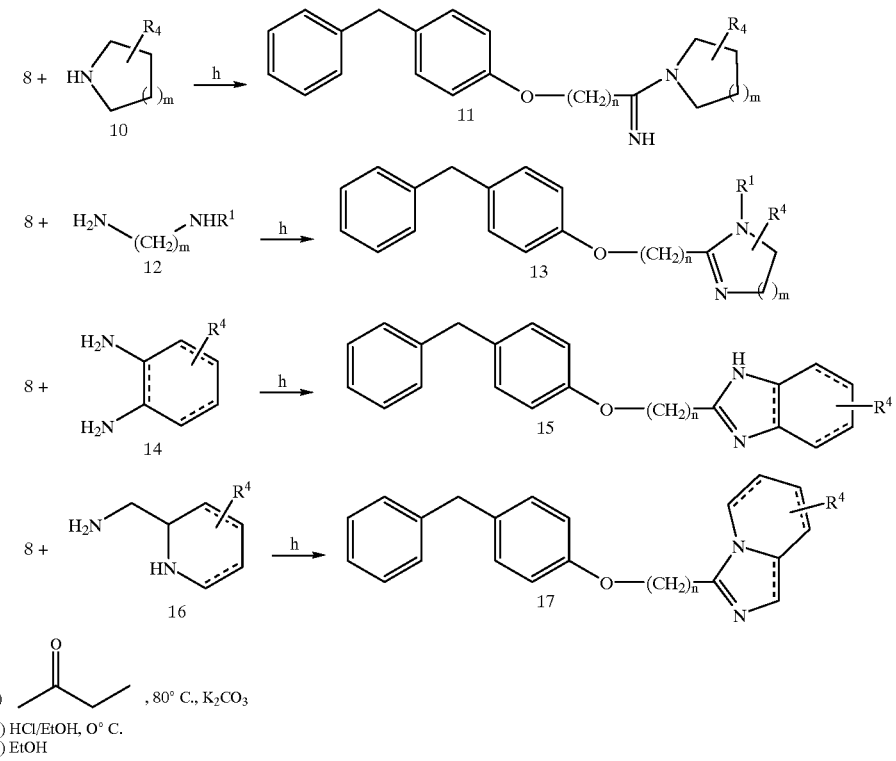

f) 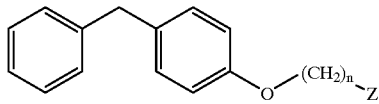 , 80° C., K₂CO₃ g) HCl/EtOH, O° C.
h) EtOH

Scheme 2 shows methods for preparing compounds having the general formula:

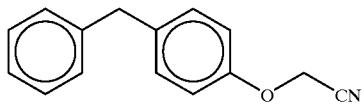

wherein Z and n are as defined hereinbefore.

4-hydroxydiphenylmethane may be reacted with an alkylnitrile halide of compound 6 in the presence of a base, for example, $K_2CO_3$, in a solvent, for example, methyl ethyl ketone, and reflux at 80° C. for 18 hours to yield compound 7. Addition of dry hydrogen chloride to compound 7 in ethanol may provide imidates, compound 8. Compound 8 may be reacted with ammonia or primary or secondary amines, in ethanol, to afford amidines, compound 9. Compound 8 may be also reacted with compounds 10, 12, 14 and 16 to generate corresponding compounds 11, 13, 15 and 17, wherein $R^1$, $R^2$, $R^4$, n and m are as defined hereinbefore.

EXAMPLE 1

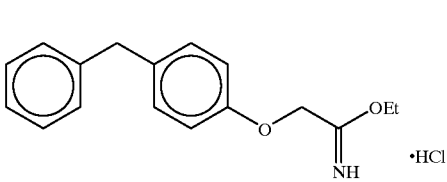

To a stirred solution of 4-hydroxydiphenylmethane (20 g, 0.11 mol) in methyl ethyl ketone (100 mL) was added chloroacetonitrile (8.3 g, 0.11 mol) and potassium carbonate (50 g, 0.36 mol) and the mixture was refluxed at 80° C. for 18 hours. The solvent was removed under reduced pressure. The residue was taken up in water, extracted twice with ether and the combined organic layers were washed 4 times with 50 NaOH, water and brine, and then dried ($Na_2SO_4$) and concentrated in vacuo to give the title compound as brown oil (23.5 g). The resulting product was fully characterized in the next step (Example 2).

EXAMPLE 2

To a stirred solution of the compound of Example 1 (23.5 g, 0.1 mol) in chloroform (60 mL) was added absolute ethanol (5 g, 0.11 mol) and the solution was cooled in the reaction flask on an ice bath. A stream of hydrogen chloride gas was introduced into the reaction mixture until the required amount of HCl (4 g, 0.11 mol) was absorbed. The flask was tightly sealed and stored in the refrigerator overnight. A white solid was filtered and washed several times with ether and then recrystalized from ethanol/ether to afford the title compound as white crystals (15 g). The product had the following properties:

Analysis calculated for $C_{17}H_{20}NO_2Cl+0.3H_2O$: Calc: C, 65.61; H, 6.67; N, 4.50. Found: C, 65.63; H, 6.41; N, 4.47.

EXAMPLE 3

α[[4-(phenylmethyl)phenoxy)methyl]-1-pyrrolidinemethanimine, monohydrochloride

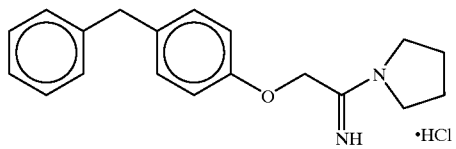

To a solution of the compound of Example 2 (1 g, 3.3 mmol) in ethanol (5 mL) was added pyrrolidine (306 mg, 4.3 mmol) and the mixture was stirred at room temperature overnight. The solvent was removed under reduced pressure and the solid was recrystallized from ethanol/ether to give the title compound as white crystals (520 mg). The product had the following properties:

Analysis calculated for $C_9H_{23}N_2OCl+0.3H_2O$: Calc: C, 67.87; H, 7.07; N, 8.33. Found: C, 67.91; H, 6.93; N, 8.27.

EXAMPLE 4

α[[4-(phenylmethyl)phenoxy)methyl]-1-peperidinemethanimine, monohydrochloride

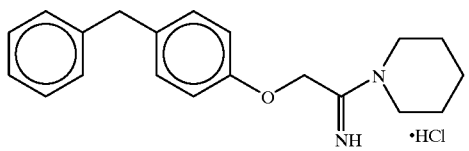

This compound was prepared by the method given in Example 3 using piperdine in place of pyrrolidine to afford the title compound as white crystals. The product had the following properties:

Analysis calculated for $C_{20}H_{25}N_2OCl$: Calc: C,69.65; H, 7.31; N, 8.12. Found: C,69.29; H, 7.12; N, 7.93.

EXAMPLE 5 ethyl 1-[1-imino-2-[4-(phenylmethyl)phenoxy]ethyl]-4-piperidinecarboxylate, monohydrochloride

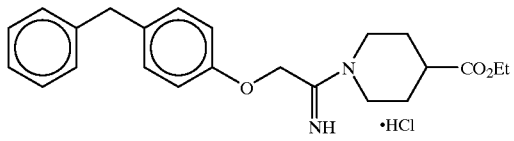

This compound was prepared by the method given in Example 3 using ethyl isonipecotate in place of pyrrolidine to afford the title compound as white crystals. The product had the following properties:

Analysis calculated for $C_{23}H_{29}N_2O_3Cl$: Calc: C, 66.26; H, 7.01; N, 6.72. Found: C, 65.86; H, 6.98; N, 6.63.

EXAMPLE 6 ethyl 3-[[1-imino-2-[4-(phenylmethyl)phenoxy]ethyl]amino]propanoate, monohydrochloride

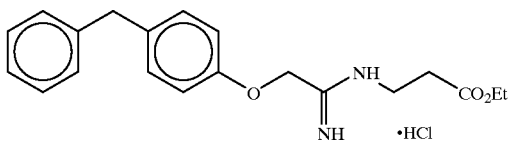

To a solution of the compound of Example 2 (0.5 g, 1.6 mmol) in ethanol (5 mL) was added beta-alanine ethyl ester hydrochloride (307 mg, 2.0 mmol) and triethylamine (202 mg, 2 mmol). The reaction mixture was stirred at room temperature overnight. The solvent was removed under reduced pressure. The residue was dissolved in ethanol and ether was added until a white solid formed. The mixture was filtered and the filtrate was concentrated and purified by preparatory silica gel plates eluting with $CHCl_3/EtOH/NH_4OH$ (84/15/1) to give the title compound as white crystals (30 mg). The product had the following properties:

Analysis calculated for $C_{20}H_{25}N_2O_3Cl+0.9 H_2O$: Calc: C, 61.11; H, 6.87; N, 7.13. Found: C, 61.04; H, 6.38; N, 7.27.

EXAMPLE 7

4,5-dihydro-2-[[4-(phenylmethyl)phenoxy]methyl]-1H-imidazole

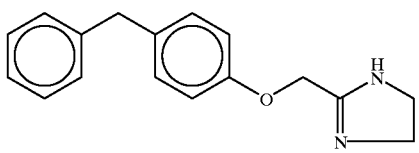

To a stirred solution of the compound of Example 2 (0.5 g, 1.6 mmol) in ethanol (5 mL) was added ethylenediamine (1 mL). The mixture was refluxed under argon for 8 hours and then cooled to room temperature. The solvent was removed under reduced pressure and the residue was dissolved in methanol. Ether was added until a white percipitate formed which was filtered, and the filtrate was concentrated and then purified by preparatory silica gel plates eluting with $CHCl_3/EtOH/NH_4OH$ (84/15/1) to give the title compound as a white solid (180 mg). The product had the following properties:

Analysis calculated for $C_{17}H_{18}N_2O+0.5 H_2O$: Calc: C, 74.16; H, 6.95; N, 10.17. Found: C, 74.01; H, 6.69; N, 10.10.

EXAMPLE 8

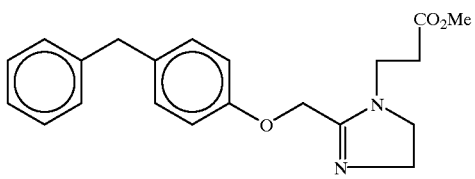

To a solution of the compound of Example 7 (70 mg, 0.26 mmol) in $CH_2Cl_2$ (2 mL) was added methyl acrylate (27 mg, 0.31 mmol). The mixture was stirred at room temperature overnight. The solvent was removed under reduced pressure and the residue was purified by preparatory silica gel plates eluting with CHCl$_3$/EtOH/NH$_4$OH (90/10/0.5) to afford the title compound as yellow oil (15 mg). The product had the following properties:

Analysis calculated for C$_{21}$H$_{24}$N$_2$O$_3$+1.1 H$_2$O: Calc: C, 67.76; H, 7.09; N, 7.53. Found: C, 67.75; H, 6.96; N, 7.50.

EXAMPLE 9

1-[1-imino-2-[4-(phenylmethyl)phenoxy]ethyl]-4-piperidinecarboxamide

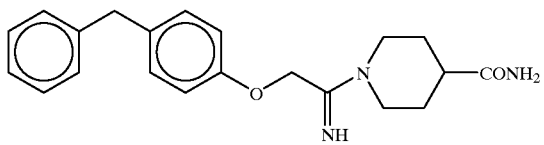

To a stirred solution of the compound of Example 2 (305 mg, 1 mmol) in ethanol (3 mL) and methanol (3 mL) was added isonipecotamide (128 mg, 1 mmol). The mixture was refluxed under argon overnight. Then the reaction mixture was cooled to room temperature and the solvent was removed under reduced pressure. The residue was dissolved in 1N NaOH and extracted three times with CH$_2$Cl$_2$. The combined organic layers were washed with water, brine, dried (Na$_2$SO$_4$), filtered and concentrated in vacuo. The solid was recrystallized from methanol/ether to give the title compound as white crystals (80 mg). The product had the following properties:

Analysis calculated for C$_{21}$H$_{25}$N$_3$O$_2$+0.3 H$_2$O: Calc: C, 70.68; N, 7.23; N, 11.78. Found: C, 70.82; H, 6.60; N, 11.82.

EXAMPLE 10

1-imino-2-[4-(phenylmethyl)phenoxy]ethanamine

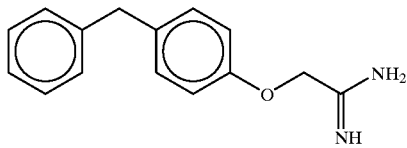

To a solution of the compound of Example 2 (305 mg, 1 mmol) in ethanol (3 mL) was added a solution of 9% NH$_3$ in ethanol (0.3 mL), and the mixture was stirred at room temperature overnight. The mixture containing a white precipitate was filtered and the filtrate was concentrated. The residue was dissolved in 1N NaOH and extracted three times with CH$_2$Cl$_2$. The combined organic layers were washed with water and brine, dried (Na$_2$SO$_4$), filtered and concentrated in vacuo. The white solid obtained was triturated with ether to give pure title compound which had the following properties:

Analysis calculated for C$_{15}$N$_{16}$N$_2$O+0.1 H$_2$O: Calc: C, 74.42; H, 6.74; N, 11.57. Found: C, 74.51; H, 6.67; N, 11.49.

EXAMPLE 11

2-[4-(phenylmethyl)phenoxy]-N-(tricyclo[3.3.1.1 3,7]decan-2-yl)ethanimidamide, monohydrate

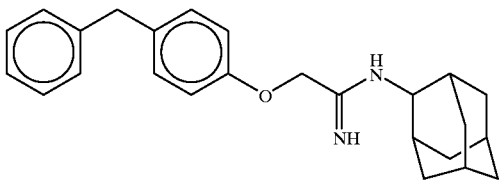

To a solution of the compound of Example 2 (458 mg, 1.5 mmol) in ethanol (10 mL) was added 2-adamantanamine hydrochloride (281 mg, 1.5 mmol) and triethylamine (152 mg, 1.5 mmol), and the mixture was stirred at room temperature overnight. The solvent was removed under reduced pressure and the residue was chromatographed on silica gel eluting with CHCl$_3$/EtOH/NH$_4$OH (92/7/0.5) to give the title compound as yellow solid (320 mg). The product had the following properties:

Analysis calculated for C$_{25}$H$_{30}$N$_2$O+1H$_2$O: Calc: C, 76.50; H, 8.22; N, 7.14. Found: C, 76.43; H, 7.90; N, 7.11.

EXAMPLE 12

N'-hydroxy-2-[4-(phenylmethyl)phenoxy]ethanimidamine

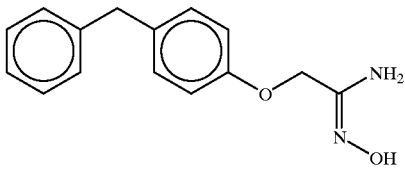

To a stirred solution of the compound of Example 1 (1 g, 4.5 mmol) in ethanol (20 mL) was added hydroxylamine hydrochloride (312 mg, 4.5 mmol) and triethylamine (454 mg, 4.5 mmol) and the mixture was refluxed for 4 hours. The mixture was cooled to room temperature and the solvent was removed under reduced pressure. The residue was dissolved in water and extracted three times with ether. The combined organic layers were dried (Na$_2$SO$_4$), filtered and concentrated in vacuo. The residue was chromatographed on silica gel eluting with hexane/ethyl acetate (4/1) to give the title compound as yellow crystals. (0.5 g). The product had the following properties:

Analysis calculated for C$_{15}$H$_6$N$_2$O$_2$: Calc: C, 70.29; H, 6.29; N, 10.93. Found: C, 70.51; H, 6.30; N, 10.81.

EXAMPLE 13

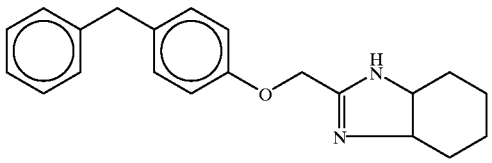

To a stirred solution of the compound of Example 2 (0.5 g, 1.6 mmol) in ethanol (5 mL) was added 1,2- diaminocyclohexane (182 mg, 1.6 mmol) and the mixture was refluxed for 5 hours. The mixture was cooled to room temperature and the solvent was removed under reduced pressure. The residue was purified by preparatory silica gel plates eluting with $CHCl_3/EtOH/NH_4OH$ (90/10/1) to give the title compound as yellow oil (100 mg). The product had the following properties:

Analysis calculated for $C_{2l}H_{24}N_2O+0.9\ H_2O$: Calc: C, 74.92; H, 7.72; N, 8.32. Found: C, 74.82; H, 7.77; N, 8.24.

EXAMPLE 14

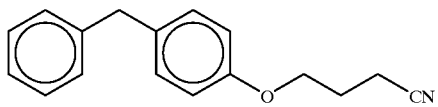

The method described in Example 1 was employed, except that 4-bromobutyronitrile was used in place of chloroacetonitrile, to afford the title compound as a yellow oil. The resulting product was fully characterized in the next step (Example 15).

EXAMPLE 15

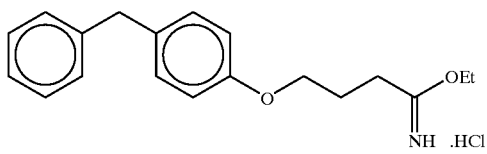

The method described in Example 2 was carried out using the compound of Example 14 in place of the compound of Example 1 to afford the title compound as white crystals. The product had the following properties:

Analysis calculated for $C_{19}H_{24}NO2Cl$: Calc: C, 68.36; H, 7.25; N, 4.20. Found: C, 68.43; H, 6.90; N, 4.10.

EXAMPLE 16

α-[3-[4-(phenylmethyl)phenoxy)propyl]-1-peperidinemethanimine, monohydrochloride

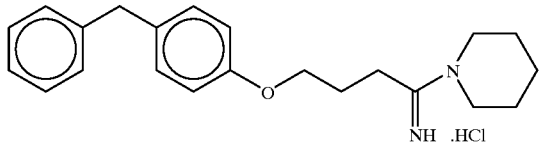

The method described in Example 3 was carried out using the compound of Example 15 in place the compound of Example 2 to afford the title compound as white crystals. The product had the following properties:

Analysis calculated for $C_{22}H_{29}N_2OCl$: Calc: C, 70.85; H, 7.84; N, 7.51. Found: C, 70.59; H, 7.90; N, 7.61.

EXAMPLE 17

4,5-dihydro-2-[[4-(phenylmethyl)phenoxy]methyl]-1H-imidazole

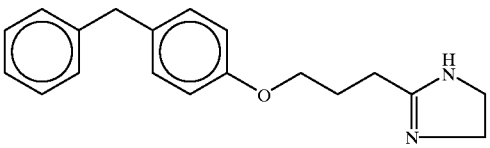

To a stirred solution of the compound of Example 15 (0.5 g, 1.5 mmol) in ethanol (5 mL) was added ethylenediamine (1 mL) and the mixture was refluxed under argon for 8 hours. The mixture was cooled to room temperature and the solvent was removed under reduced pressure. The residue was dissolved in 5% $K_2CO_3$ and extracted three times with $CH_2Cl_2$. The combined organic layers were washed with water and brine, dried with $Na_2SO_4$, filtered and concentrated in vacuo. The residue was purified by preparatory silica gel plates eluting with 2% $NH_4OH/MeOH$ to give the title compound as yellow solid (50 mg). The product had the following properties:

Analysis calculated for $C_{19}H_{22}N_2O+0.4\ H_2O$: Calc: C, 75.67; H, 7.62; N, 9.29. Found: C, 75.68; H, 7.58; N, 9.20.

LTA Hydrolase Methods

The following Table presents data demonstrating the pharmacological activity of the LTA hydrolase inhibitors of the present invention. One or more of three different assays, (1) an in vitro LTA hydrolase enzyme assay, (2) a human whole blood assay utilizing calcium ionophore stimulation, and (3) a murine ex vivo assay utilizing calcium ionophore stimulation were employed to determine the level of LTA hydrolase inhibitor activity.

Recombinant Human LTA Hydrolase Assay for LTA Hydrolase Inhibitor Activity

Compounds of the present invention were tested for LTA hydrolase inhibitor activity against recombinant human LTA hydrolase (rhLTAH). Recombinant human LTA hydrolase-encoding vectors were prepared and used to express rhLTAH essentially as described by J. Gierse, et al., *Protein Expression and Purification*, 4, 358–366 (1993). Briefly, LTA hydrolase encoding DNA was amplified by polymerase chain reaction using a pair of oligonucleotide primers based on the nucleotide sequence from the 5'-end, and the complement of the 3'-end, of the coding region of the LTA hydrolase gene, the nucleotide sequence of which gene is known. (See, C. Funk, et al., Proc. Natl. Acad. Sci. U.S.A. 84, 6677–6681 (1987)). A λgt11 human placental cDNA library (Clonetech, Palo Alto, Calif.) provided the nucleic acid template. The LTA hydrolase encoding region had a length of about 1.9 kb. The amplified 1.9 kb DNA was isolated and cloned into the genomic baculovirus, *Autographa californica* nuclear polyderosis virus (AcNPC) DNA, and the baculovirus expression vector was transfected into Spodoptera frugiperda Sf-9 cells employing the calcium phosphate co-precipitation method (see, M. Summers, et al., Tex. Agric. Exp. Stn. Bull. 1555, 1–57 (1987). Recombinant $LTA_4$ hydrolase enzyme was purified from the transfected Sf-9 cells essentially as described by J. Gierse, et al., supra.

One or more predetermined amounts of a compound of the invention were incubated in assay buffer (0.1 M potassium phosphate, 5 mg/ml fatty acid free BSA, 10% DMSO, pH 7.4) for 10 minutes at room temperature with 250 ng of recombinant hLTA$_4$H to allow binding, if any, between the enzyme and inhibitor. The stock enzyme solution was 1 mg/m. LTA$_4$ hydrolase, 50 mM Tris, pH 8.0, 150 mM NaCl, 2.5 mM beta-mercaptoethanol, 50% glycerol. The specific activity of the enzyme was about 650 nMoles/min/mg. LTA$_4$ (i.e., substrate) was prepared from the methyl ester of LTA, (Biomol, Inc., Plymouth Meeting, Pa.) by treating the methyl ester with 30 molar equivalents of LiOH at room temperature for 18 hours. The LTA$_4$ substrate in its free acid form was kept frozen at −80° C. until needed. LTA, (free acid) was thawed and diluted in assay buffer (minus DMSO) to a concentration of 350 ng/ml and 25 μl (8 ng) of LTA$_4$ substrate was added to the reaction mixture (total volume of reaction mixture=200 μl at time zero. Each reaction was carried out at room temperature for 10 minutes. The reaction was stopped by diluting 25 μl of the reaction mixture with 500 μl of the assay buffer without DMSO. LTA$_4$ was quantified in the diluted sample by a commercially available enzyme-linked immunoassay [Caymen Chemical Col. Ann Arbor, Mich.] using the method recommended in the manufacturer's instructions and compared to the amount of LTA$_4$ produced in a negative control (i.e., essentially identical conditions except without addition of an inhibitor compound). The IC$_{50}$ was routinely calculated from the data produced.

LTB$_4$ and Thromboxane Production by Calcium Ionophore Stimulated Human Blood for LTB$_4$ Hydrolase Inhibitor Activity Human blood, collected in heparin-containing Vacutainer tubes, was diluted 1:4 with RPMI-1640 media and 200 μl of the diluted blood was added into each of a 96-well microtiter plate. One or more concentrations of the leukotriene A$_4$ hydrolase inhibitor compounds being tested were prepared (diluted in DMSO) and 2 μl added and gently mixed with the diluted whole blood. After incubating for 15 minutes at 37° C. in a humidified incubator, calcium ionophore A13187 (Sigma Chemical Co., St. Louis, Mo.) was added to a final concentration of 20 mcg/ml and the incubation continued under the same conditions for an additional 10 minutes to allow LTB$_4$ formation. The reaction was terminated by centrifugation (833 g, 10 minutes at 4° C.) and supernatant were analyzed for LTB$_4$ and thromboxane by commercially available enzyme-linked immunoassays (Caymen Chemical Co., Ann Arbor, Mich.) according to the manufacturer's instructions. The IC$_{50}$ of each test compound was determined from the amount of inhibition of LTB$_4$ production as compared to an essentially identical assay in which no inhibitor compound was present.

Ex Vivo LTB$_4$ and Thromboxane Production by Calcium Ionophore Stimulated Mouse Blood for LTB$_4$ Hydrolase Inhibitor Activity Leukotriene A$_4$ hydrolase inhibitor compounds of the present invention were diluted to a predetermined concentration in phosphate buffered saline containing 2%; DMSO and 1% Tween 80. The compounds were administered by oral gavage to adult male outbred mice weighing approximately 20–30 gm at a dose of 10 mg/kg body weight. (Compounds given at a dose of 50 mg/kg body weight are designated in following Table by the symbol, *) Sixty (60) minutes after administration of an LTA$_4$ inhibitor compound of the invention, blood was collected (into heparin-containing tubes) from the retroorbital sinus. The heparinized blood was added to the wells of a microtiter plate along with an equal volume of RPMI-1640 media, and calcium ionophore A23187 was added to a final concentration of 20 mcg/ml. The mixture was incubated for 10 minutes at 37° C. in a humidified incubator. The reaction was terminated by centrifugation (833 g. 10 minutes at 4° C.). Supernatant were analyzed for LTB$_4$ and thromboxane by commercially available enzyme-linked immunoassays [Caymen Chemical Co., Ann Arbor, Mich.] in accordance with the manufacturer's instructions. The percent inhibition was determined by comparison to animals treated identically except that the solution administered by oral gavage was devoid of inhibitor compound.

LTA$_4$ Hydrolase Inhibitor Activity

| Ex. # | Recombinant Human LTA$_4$ Hydrolase Assay IC$_{50}$ LTA$_4$ (μM) | Inhibition of Calcium Ionophore-induced LTB$_4$ Production in Human Blood IC$_{50}$ HWB (μM) | Murine Ex Vivo LTB$_4$ Inhibition % I LTB$_4$/at 1 hour after administration of 10 mg/kg |
|---|---|---|---|
| 3 | 0.004 | 0.053 | 46 |
| 4 | 0.0043 | 0.085 | 30 |
| 5 | 0.0013 | 0.071 | 62 |
| 6 | 0.023 | 0.2 | 54 |
| 7 | 0.07 | 0.22 | 33 |
| 8 | 1.17 | 0.55 | 68 |
| 9 | 0.017 | 0.077 | 30 |
| 10 | 0.089 | 0.48 | 0 |
| 11 | 7.8 | — | — |
| 12 | >100 | 17.9 | 63 |
| 13 | 0.2 | 0.19 | 71 |
| 16 | 0.053 | 0.64 | 60 |
| 17 | 0.064 | 0.64 | 28 |

"—" means Not Determined

What is claimed is:
1. A compound selected from the group consisting of:

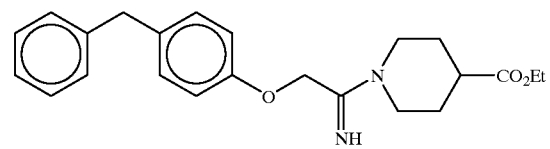

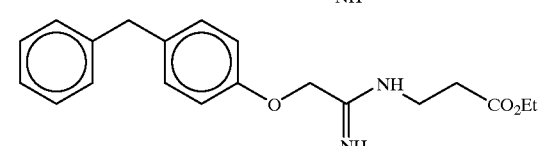

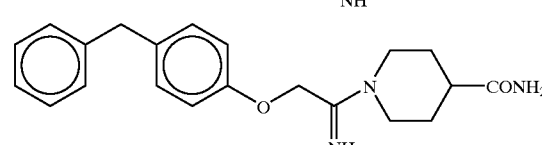

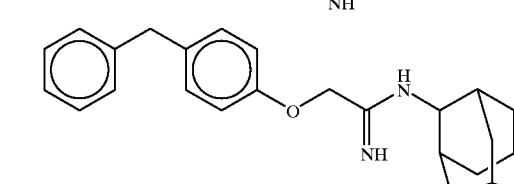

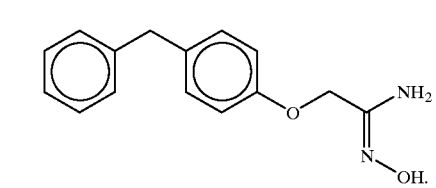

2. A pharmaceutical composition comprising a compound selected from the group consisting of:

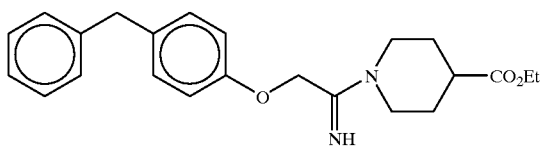
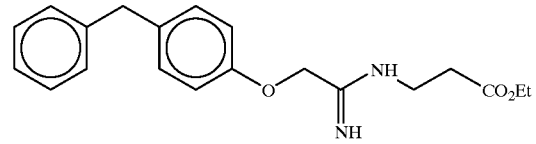
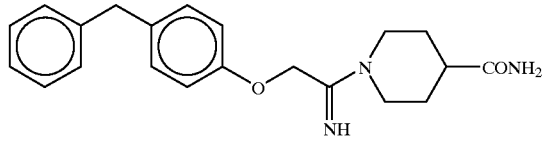
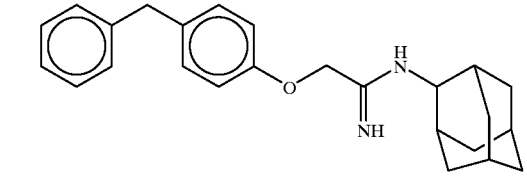
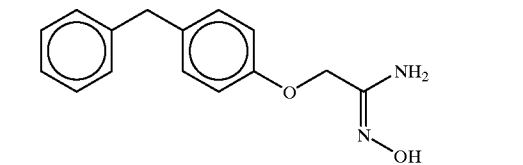

pharmaceutically acceptable salts and stereoisomers thereof, and combinations of said compounds, pharmaceutically acceptable salts and stereoisomers thereof, and a pharmaceutically acceptable carrier.

3. A method for treating an LTB$_4$-mediated inflammatory disease comprising administering to a mammal in need of treatment a therapeutically effective amount of a compound selected from the group consisting of:

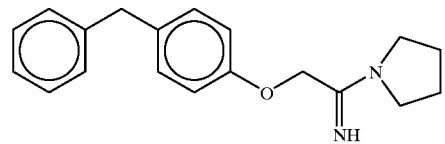
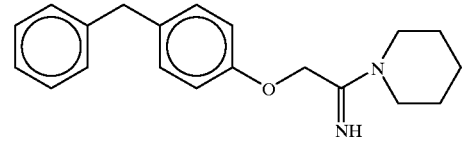
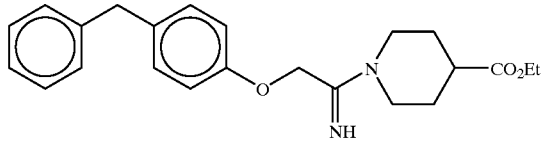

-continued

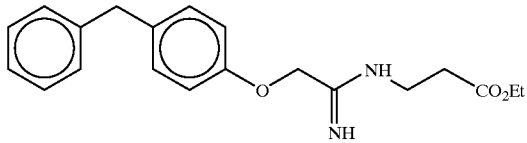
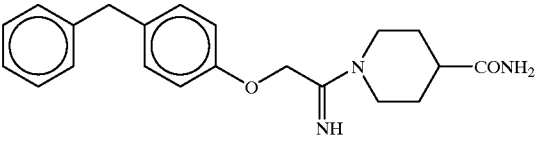
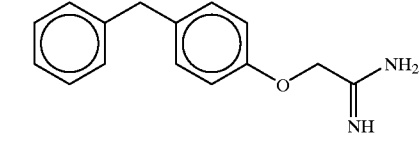
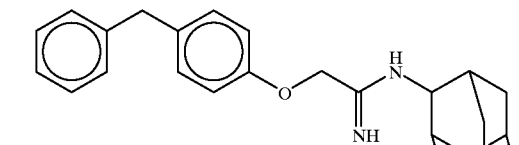
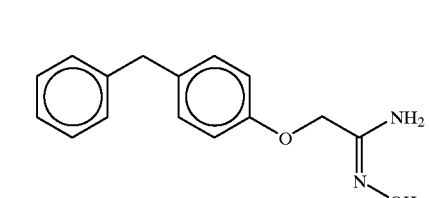

and

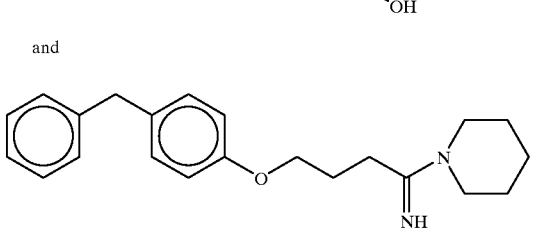

pharmaceutically acceptable salts and stereoisomers thereof, and combinations of said compounds, pharmaceutically acceptable salts and stereoisomers thereof.

4. The method of claim 3 wherein the compound, pharmaceutically acceptable salt or stereoisomers thereof, combinations of said compounds, pharmaceutically acceptable salts and stereoisomers thereof, is administered as a pharmaceutical composition further comprising a pharmaceutically acceptable carrier.

* * * * *

UNITED STATES PATENT AND TRADEMARK OFFICE
CERTIFICATE OF CORRECTION

PATENT NO. : 6,110,944
DATED : August 29, 2000
INVENTOR(S) : Barbara B. Chen et al.

It is certified that error appears in the above-identified patent and that said Letters Patent is hereby corrected as shown below:

Title page,
Item [54], in the title, "LTA4," should read -- $LTA_4$ --.
Item [56], References Cited, FOREIGN PATENT DOCUMENTS, "287959 10/1988 European Pat. Off. ." (second occurrence) should be deleted.

Column 1,
Line 1, "LTA4," should read -- $LTA_4$ --.

Column 2,
Line 7, "$Ar^1$" should read -- $Ar_1$ --;
Line 38, "$Ar^2$" should read -- wherein $R_7$, $R_8$ and $R_9$ are individually Cl, Br, F, $CF_3$, lower alkyl, lower alkoxy, $NH_2$, $NO_2$, and OH; ¶ $Ar_2$ --;
Line 53, "$-CF_2-m$" should read -- $-CF_2-$, --.

Column 3,
Line 16, "========== represents" should read -- ---------------- represents -- ;
Line 52, "LTB4 mediated" should read -- $LTB_4$-mediated --.

Column 4,
Line 16, "included," should read -- include, --.

Column 5,
Line 9, "disintigrating" should read -- disintegrating --;
Line 16, "Disintigrators" should read -- Disintegrators --.

Column 10,
Line 35, "50 NaOH, " should read -- 5% NaOH, --;
Line 61, "recrystalized" should read -- recrystallized --.

Column 11,
Line 23, "$C_9H_{23}N_2OCl$" should read -- $C_{19}H_{23}N_2OCl$ --.
Line 66, "$C_{23}H_{29}N_2O_3Cl$: should read -- $C_{23}H_{29}N_2O_3Cl$: --.

Column 13,
Line 66, "$C_{15}N_{16}N_2O+0.1\ H_2O$:" should read -- $C_{15}N_{16}N_2O+0.1\ H_2O$: --.

UNITED STATES PATENT AND TRADEMARK OFFICE
CERTIFICATE OF CORRECTION

PATENT NO.    : 6,110,944
DATED         : August 29, 2000
INVENTOR(S)   : Barbara B. Chen, et al.

It is certified that error appears in the above-identified patent and that said Letters Patent is hereby corrected as shown below:

Column 15,
Line 9, "$C_{21}H_{24}N_2O+0.9\ H_2O$:" should read $C_{21}H_{24}N_2O+0.9\ H_2O$: --;
Line 43, "$C_{19}H_{24}NO2CL$: should read -- $C_{19}H_{24}NO_2CL$: --.
Line 50, "peperidinemethanimine," should read -- piperidinemethanimine, --.

Column 17,
Line 6, "LTA," should read -- $LTA_4$ --;
Line 10, "LTA," should read -- $LTA_4$ --;
Line 14, "$200\mu 1$" should read -- $200\mu 1$) --;
Line 54, "2%;" should read -- 2% --.

Signed and Sealed this

Fifth Day of February, 2002

Attest:

Attesting Officer

JAMES E. ROGAN
*Director of the United States Patent and Trademark Office*